（12）United States Patent
Pei et al.

(10) Patent No.: US 8,694,082 B2
(45) Date of Patent: Apr. 8, 2014

(54) METHOD AND SYSTEM FOR DETECTING AND TREATING JUNCTIONAL RHYTHMS

(75) Inventors: Xing Pei, Thousand Oaks, CA (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 895 days.

(21) Appl. No.: 12/727,130

(22) Filed: Mar. 18, 2010

(65) Prior Publication Data
US 2011/0230927 A1 Sep. 22, 2011

(51) Int. Cl.
*A61B 5/0452* (2006.01)

(52) U.S. Cl.
USPC .......................................... 600/515

(58) Field of Classification Search
USPC .................................. 600/509, 515
See application file for complete search history.

(56) References Cited

U.S. PATENT DOCUMENTS

| 6,493,583 B1 | 12/2002 | Levine et al. |
| 6,748,270 B2 | 6/2004 | Rouw et al. |
| 7,236,824 B2 | 6/2007 | Rouw et al. |
| 2002/0161409 A1 | 10/2002 | Rouw et al. |
| 2004/0210262 A1 | 10/2004 | Rouw et al. |

OTHER PUBLICATIONS

Barold, S. Serge et al., "Pacemaker Repetitive Nonreentrant Ventriculoatrial Synchronous Rhythm. A Review," Journal of Interventional Cardiac Electrophysiology. 2001;5:45-58.

Levine, Paul A. MD, FHRS, FACC, "Pacemaker Mediated Tachycardia and Repetitive Non-Reentrant Ventriculo-Atrial Synchronous Rhythm: Two Sides of the Same Phenomenon," Manuscript. May 2009:1-17.

Fisher, John D. MD, FACC et al., "Role of Implantable Pacemakers in Control of Recurrent Ventricular Tachycardia," The American Journal of Cardiology. 1982;49:194-206.

Orem, Randall C. et al., "A Novel Approach to the Management of Symptomatic Junctional and Ectopic Atrial Rhythms," Journal of Interventional Cardiac Electrophysiology. 2003;9:353-356.

*Primary Examiner* — Amanda Patton

(57) ABSTRACT

An implantable medical device is provided for detecting transportless ventricular rhythm of a heart lacking atrial transport and comprises a housing, sensors configured to be located proximate to a heart, a sensing module to sense cardiac signals representative of a rhythm originating from the heart and a rhythm detection module. The rhythm detection module determines a change in AV association and identifies a potential ventricular complex with loss of atrial transport (VCLAT) based on the change in AV association.

19 Claims, 13 Drawing Sheets

METHOD AND SYSTEM FOR DETECTING AND TREATING JUNCTIONAL RHYTHMS

BACKGROUND OF THE INVENTION

Embodiments of the present invention generally relate to loss of atrial transport in the heart, and more specifically to methods and systems for detecting, treating and collecting diagnostic data regarding accelerated junction rhythms (AJR) and accelerated idioventricular ventricular rhythms (AIVR).

Implantable medical devices are well known in the art. They include implantable pacemakers which provide stimulation pulses to a heart to cause a heart, which would normally or otherwise beat too slowly or at an irregular rate, to beat at a controlled normal rate. They also include cardioverters and defibrillators which detect when the atria and/or the ventricles of the heart are in tachycardia arrhythmia or fibrillation, and apply anti-tachycardia pacing therapy and/or cardioverting or defibrillating electrical energy to the heart to restore the heart to a normal rhythm. Implantable medical devices may also include the combined functionalities of a pacemaker and a defibrillator.

Implantable medical devices sense cardiac activity for monitoring the cardiac condition of the patient in which the device is implanted. By sensing the cardiac activity of the patient, the device is able to provide cardiac stimulation therapy when it is required. In a healthy heart, the sinoatrial node (SA node) serves as the natural pacemaker of the heart. It is a group of specialized myocardial cells located on the posterior wall of the upper right atrium at the junction between the atrium and the superior vena cava. It initiates electrical impulses in the heart's myocardium at a more rapid rate than other myocardial cells.

The atrioventricular node (AV node) transmits electrical signals from the atria to the ventricles. It is a small concentration of specialized conductive tissue at the base of the atrial septum. The AV node serves an important role in maintaining atrioventricular synchrony, the sequence of an atrial depolarization followed by a ventricular depolarization after an appropriate conduction time (AS-VS interval). Maintenance of atrioventricular synchrony enhances cardiac output and the loss of it (loss of atrial transport) reduces cardiac output. If the SA node fails, the AV node is capable of serving as an intrinsic back-up pacemaker of the heart. However, the cardiac rate, under such circumstances, is generally lower than normal (40 to 60 beats per minute) and is without atrial transport. In special circumstances, the junctional pacemaker may accelerate and usurp control from an otherwise normal sinus node. In the setting of sinus node dysfunction for which a single-chamber atrial or a dual-chamber pacemaker was implanted, the junctional focus may accelerate and usurp control from the otherwise normally functioning pacemaker.

Accelerated junctional rhythms may occur as a consequence of AV nodal ablation, intrinsic disease involving the atrioventricular node also called the AV junction and commonly labeled "junctional pacemaker" or "junctional focus", as a consequence of metabolic imbalance or as a side effect of a multiplicity of medications.

Hence, patients with SA node dysfunction or who have had their AV node ablated generally have a demand pacemaker to regulate their heart rhythm. While such devices do regulate cardiac rhythm, these patients can experience accelerated junctional rhythms which may then inhibit the artificial pacemaker. While the normal rate of a junctional focus is between 40 to 60 bpm and is dominated by the sino-atrial node which commonly discharges at a more rapid rate (60 to 100 bpm), the accelerated junctional rhythm (AJR) may occur at faster rates than normal and usurp control from the sinus node. The junctional rates accelerate due to a multiplicity of causes including intrinsic disease in the junctional focus, parasympathetic withdrawal or increased sympathetic stimulation. When this focus usurps control from the sinus node or the pacemaker, the faster intrinsic rhythm will be sensed by the pacemaker causing it to inhibit. The result is a loss of atrial transport. This abnormal rhythm may be associated with retrograde conduction to the atrium. In both circumstances, hemodynamics may be compromised resulting in significant symptoms for the patient. Also, under these conditions, the implanted demand pacemakers may be unable to provide assistance as the higher rate of the junctional focus may cause the pacemaker or ICD to be inhibited.

A similar rhythm, but arising from a ventricular focus, is termed accelerated idioventricular rhythm (AIVR). It will have similar consequences with respect to compromising hemodynamics and for the patient who has a dual-chamber pacemaker, result in its inhibition. This rhythm may also be associated with retrograde conduction.

As a group, these rhythms may be labeled as a ventricular complex with loss of atrial transport VCLAT. Hence, functionally, a third VCLAT is sinus rhythm with a marked first degree AV block. In the absence of pacing, a marked first degree AV block may allow the native P wave to coincide with the previous ST-T wave associated with the conducted R wave limiting or even eliminating atrial transport (atrial contraction contributing to ventricular filling) resulting in an under-filled ventricle, a drop in stroke volume and cardiac output and the atria contracting against a closed mitral and tricuspid valve forcing system and pulmonary congestion. In the setting of a dual-chamber pacemaker, this can result in a rhythm labeled Repetitive Non-Reentrant Ventriculo-Atrial Synchrony (RNRVAS) where the native P-wave coincides with the Post-Ventricular Atrial Refractory Period (PVARP) thus allowing for delivery of an atrial output pulse. The atrial output pulse itself is ineffective because the atrial tissue is physiologically refractory in response to the native P wave. During episodes of accelerated junctional rhythms (AJR) or an accelerated idioventricular rhythm (AIVR), there will be a loss of atrial transport and even retrograde conduction. The patients may become symptomatic. This is not uncommon in patients with sinus node dysfunction. The junctional focus responds to increases in sympathetic tone, caused by, for example, physical exertion or any etiology of stress including emotional upset. Throughout the present application, AJR, AIVR and first degree AV block will be collectively referred to as ventricular complex with loss of atrial transport or VCLAT. AIVR rhythms occur in association with other disease states involving the ventricle such as cardiomyopathy, ischemic heart disease and as a side-effect of various medications. As such, an acceleration of the junctional rhythm (meaning both rhythms) may occur at physical rest and/or exercise. Present generation implantable medical devices (pacemaker or ICD) do not have a unique algorithm to detect, treat and collect diagnostic data for patients with VCLAT rhythms (AJR or AIVR or marked first degree AV block).

In each of the above discussed rhythms, there is an intrinsic ventricular depolarization effectively inhibiting the pacemaker; yet each is associated with the loss of an optimal AV delay compromising cardiac function.

SUMMARY

In accordance with embodiments, VCLAT algorithms are provided that detect, treat/mitigate and collect the diagnostic information. When utilized, embodiments described herein will reduce the patient symptom and improve the quality of life of the patient.

In accordance with one embodiment, an implantable medical device is provided for detecting VCLAT rhythms of a heart lacking atrial transport and comprises a housing, sensors configured to be located proximate to a heart, a sensing module to sense cardiac signals representative of a rhythm originating from the heart and a rhythm detection module. The rhythm detection module determines a change in AV association and identifies a potential ventricular depolarization with loss of atrial transport (VCLAT) based on the change in AV association.

In an alternative embodiment, a method is provided for detecting a transportless ventricular rhythm of a heart. The method comprises sensing cardiac signals representative of a rhythm originating from the heart. The method further includes determining a change in AV association and identifying a VCLAT based on the change in AV association.

In accordance with an embodiment, an implantable cardiac stimulation device is provided for treating a transportless ventricular rhythm. The implantable device comprises a housing and sensors configured to be located proximate to a heart. The implantable cardiac stimulation device further provides a sensing module to sense cardiac signals representative of a rhythm originating from the heart. The implantable cardiac stimulation device further comprises a rhythm detection module to identify at least one of an accelerated junctional rhythm (AJR) and an accelerated idioventricular rhythm (AIVR) and further comprises a therapy control module. Optionally, the therapy control module delivers an AJR-based therapy when the rhythm detection module identifies an AJR and delivers an AIVR-based therapy when the rhythm detection module identifies an AIVR, wherein the AJR-based therapy differs from the AIVR-based therapy.

In accordance with an embodiment, a method is provided for treating a VCLAT rhythm. The method comprises sensing cardiac signals representative of a rhythm originating from the heart and identifying at least one of an accelerated junctional rhythm (AJR) and an accelerated idioventricular rhythm (AIVR). The method further comprises delivering an AJR-based therapy when the rhythm detection module identifies an AJR and delivering an AIVR-based therapy when the rhythm detection module identifies an AIVR, wherein the AJR-based therapy differs from the AIVR-based therapy.

DETAILED DESCRIPTION

Figure 1:
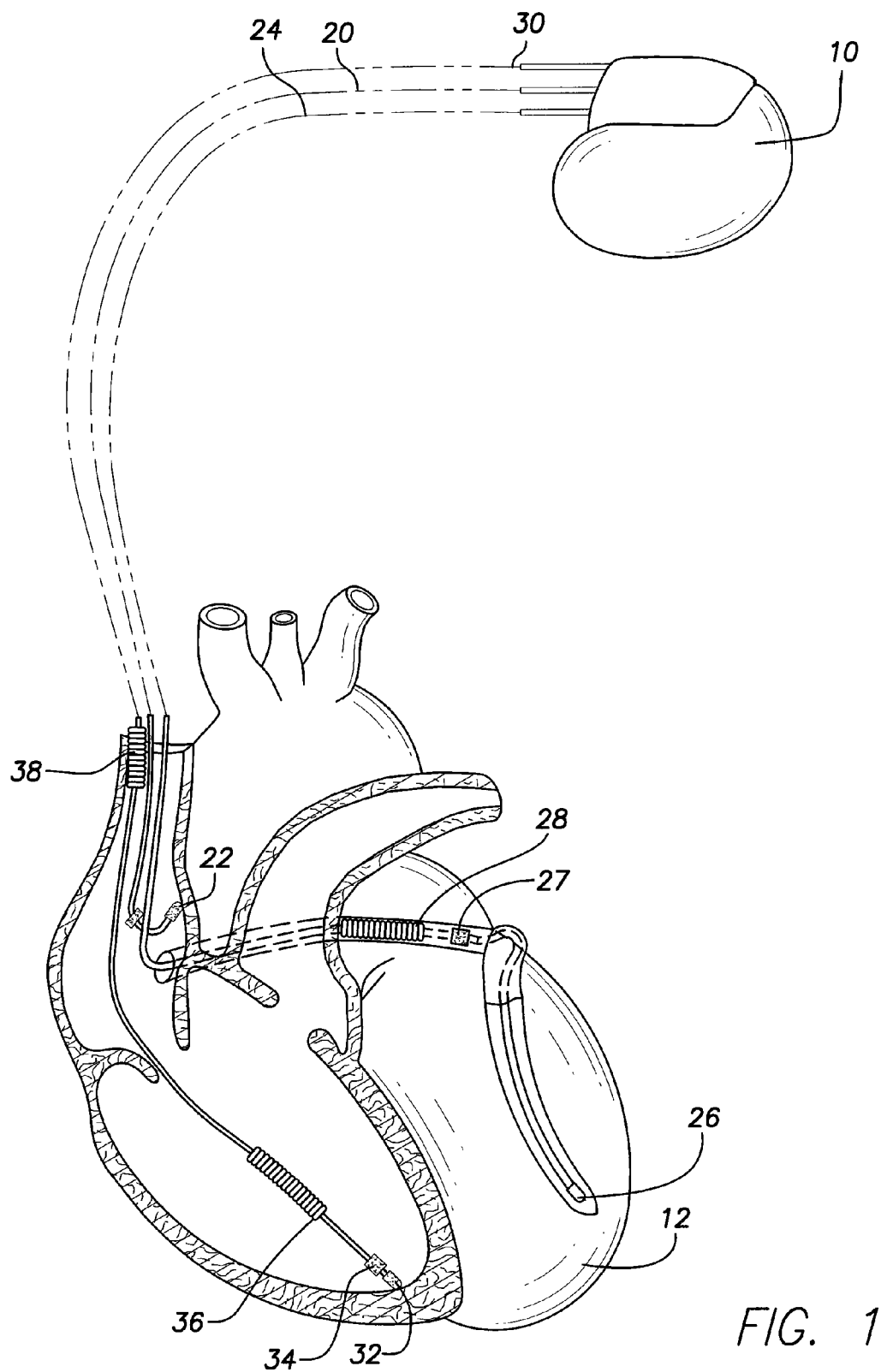
FIG. 1 illustrates an implantable medical device (IMD) 10 that is implemented in accordance with an embodiment.

The following description is of the best mode presently contemplated. This description is not to be taken in a limiting sense but is made merely for the purpose of describing embodiments of the invention. The scope of the invention should be ascertained with reference to the issued claims. In the description that follows, like numerals or reference designators will be used to refer to like parts or elements throughout.

Throughout the present application, the following abbreviations shall be utilized. The term AS shall mean atrial sensed event also labeled as a "P" Wave when looking at the surface ECG. Functionally AS and P wave are identical and do not represent a specific site of origin. The term AP shall mean atrial paced event. The term ASR shall mean atrial sensed event but occurring during the refractory period such that it does not alter any device timing. The term VS shall mean ventricular sensed event also labeled a "R" wave or "QRS" complex as recorded on a surface ECG. Functionally, VS is equivalent to R wave or QRS complex and does not represent a specific site of origin. The term VP shall mean ventricular paced event. The term VSR shall mean ventricular sensed event but occurring during the ventricular refractory period. The term VS-AP interval shall mean the interval between a sensed ventricular event and a subsequent paced atrial event. The term VS-AS interval shall mean the interval between a sensed ventricular event and a subsequent sensed atrial event.

Accelerated junctional rhythms occur with various conditions when junctional focus responds to increases in sympathetic tone, caused by, for example, physical exertion and stress. Embodiments of the present invention monitor cardiac signals and identify ventricular depolarizations with loss of atrial transport (VCLAT) based on certain traits identifiable within the intracardiac electrograms (IEGMS). For example, these traits include heart rate, R-wave morphology, AV association (e.g. AS-VS interval, VS-AS interval) and the occurrence of a P-wave before, around or after an R-wave. An accelerated junctional rhythm exhibits certain traits similar to an SVT or VT arrhythmia except it occurs at lower rate, typically between 60-99 ppm, and with narrow R-wave morphology, similar to conducted beats. If there was a bundle branch block resulting in a wide QRS complex, the junctional rhythm will also have the same morphology QRS complex as that of a sinus origin. An AJR is typically regular, and may occur with or without a sudden rate change. An AIVR and an AJR exhibit a change in the AV relationship, at rates lower than the defined VT starting rate. An AJR generally exhibits narrow morphology or a morphology similar to the conducted QRS complex, while AIVR may have a wide morphology or when the conducted QRS complex is wide, the AIVR complex is often morphologically different even when both are wide. An AJR will occur with or without an intrinsic P-wave preceding it. When the AJR complex occurs, any relationship to the P wave is coincidental and the interval between the two complexes will not be stable but will vary.

Embodiments of the present invention treat AVR with AVR-based therapy, and treat AIVR with AIVR-based therapy. An AVR may be suppressed by pacing in the atrium or broke by deliver atrial pacing at an appropriate time when the atrial pace induced excitation overtake the AJR and entrain the AJR. Atrial pacing before an AJR or AIVR induced ventricular contraction may provide atrial contraction that provides support for atrial transport. Inducing atrial contractions timed to support a VCLAT rhythm is helpful in the setting of AV block where the atrial paced beat, even at an accelerated rate, cannot be expected to conduct through the AV node and assume control of the ventricle.

The systems and methods described herein utilize the above noted traits and physiologic states to detect and classify the accelerated AJR, deliver overdrive atrial pacing to provide atrial transport support and suppress, entrain and/or break the AJR and to restore normal sinus rhythm, either paced or intrinsic. Embodiments of the present invention collect diagnostics to help physicians to make diagnosis and prescribe appropriate therapy/medicine to benefit the patient. Embodiments of the present invention are also used to mitigate some reentrance arrhythmias.

FIG. 1 illustrates an implantable medical device (IMD) 10 that is implemented in accordance with an embodiment. Although the device 10 described herein is a combined dual-chamber pacemaker and cardioverter/defibrillator having numerous leads, coil electrodes and pacing electrodes to provide both right and left heart dual-chamber pacing and atrial and ventricular cardioversion/defibrillation, it will be understood by those skilled in the art that this description is meant to illustrate the integrate ability of embodiments of the present invention into any implanted device providing dual-chamber pacing. Hence, embodiments may be employed to advantage in a dual-chamber pacing system having only atrial and ventricular unipolar electrodes or in a more sophisticated device of the type described herein. As a result, any reference to device function beyond that of dual-chamber pacing is made herein for purposes of completeness only.

The device 10 is in electrical communication with a patient's heart 12 by way of three leads, 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The electrode 22 may alternatively be positioned any place in the right atrium with the use of an active fixation lead or even in the left atrium with special leads.

To sense left atrial and ventricular cardiac signals and to provide left-chamber pacing therapy, the stimulation device 10 is coupled to a "coronary sinus" lead 24 designed for placement in the "coronary sinus region" via the coronary sinus so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Coronary sinus electrode refers specifically to left ventricular stimulation which will include epicardial leads placed directly on the surface of the left ventricle or left ventricular endocardial leads inserted via a patent foramen ovale or direct puncture of the interatrial septum.

Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Optionally, the right ventricular lead 30 may be transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. The right ventricular lead 30 is capable of receiving cardiac signals, and delivering stimulation in the form of pacing and shock therapy to the right ventricle.

Figure 3:
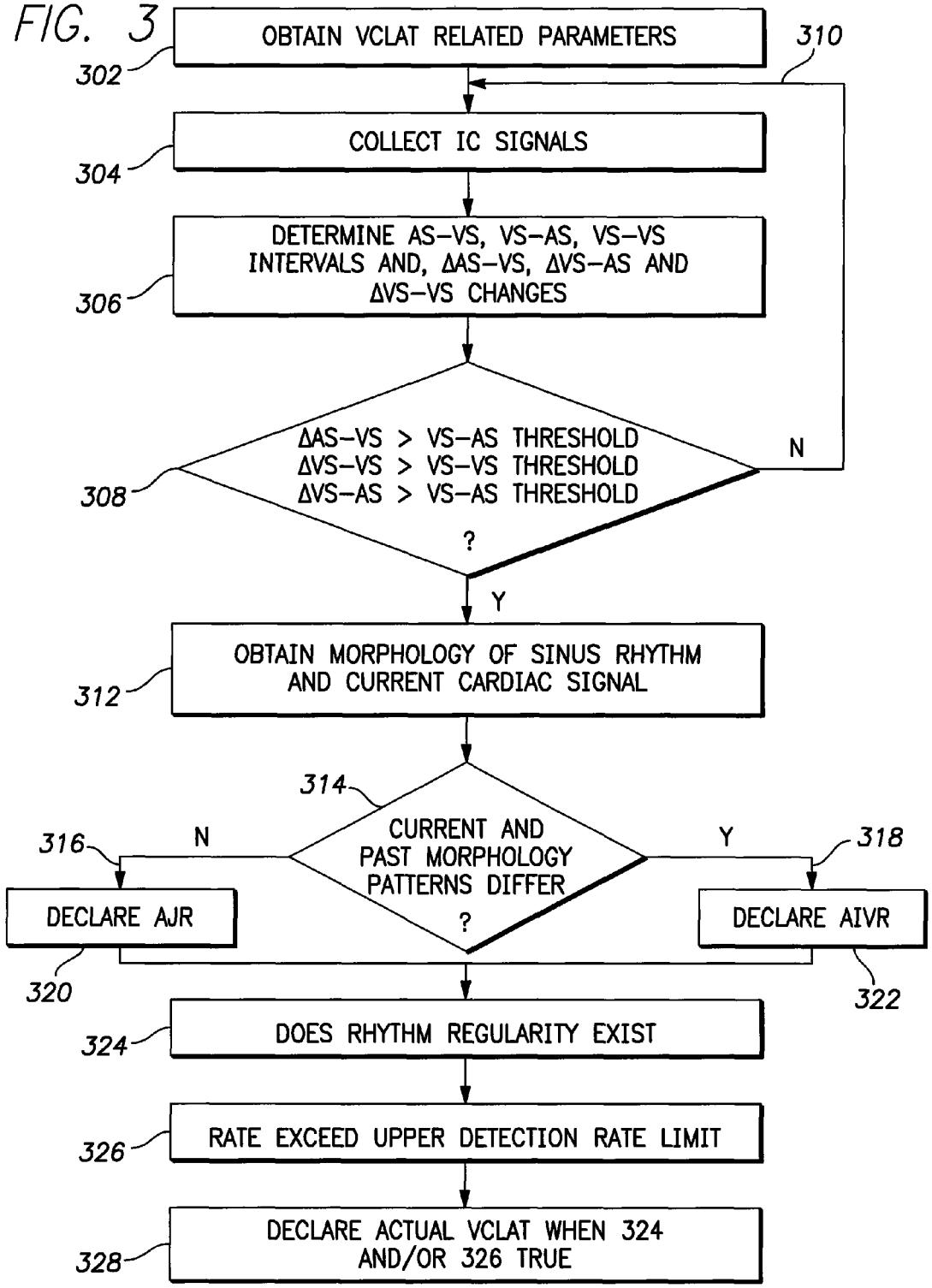
FIG. 3 illustrates a method for detecting a transportless ventricular rhythm (VTR) of a heart in accordance with an embodiment of the present invention.

FIG. 3 illustrates a method for detecting a transportless ventricular rhythm (VTR) of a heart in accordance with an embodiment of the present invention. The method of FIG. 3 may be implemented by an IMD, by an external device, by an external programmer and the like. The method begins at 302 where, during a set-up operation, the memory is accessed to obtain, among other things, programmable VCLAT-related parameters. The VCLAT-related programmable parameters include, among other things, high and low rate limits for an accelerated junctional rhythm rate detection range. For example, the low rate limit may be a base rate (e.g. 60 bpm, 75 bpm, etc.) and the high rate limit may be a start rate for the first programmed VT1 zone in an ICD or MSR in a pacemaker. For a rhythm to be declared as a potential VCLAT, the heart rate will fall between the upper and lower VCLAT rate limits. The VCLAT-related parameters also include a regularity criteria (e.g. 5-80 ms) which may be programmed in predetermined steps (e.g. 5 ms steps). The regularity criteria represent the degree of correlation between the morphology of a current rhythm and a past morphology. The past morphology may be from a past rhythm sensed and stored recently by the IMD, by an external monitor device or by an external programmer. Alternatively, the past morphology may be derived from a group of past rhythms (e.g., an average over 10-20 cardiac cycles). The past morphology may be for cardiac signals for one or more heart cycles that immediately precede a current rhythm. Alternatively, the past morphology may be for cardiac signals collected over a longer period of time before the current rhythm (e.g., from 1 minute earlier, 5 minutes earlier, 30 minutes earlier, 1 hour earlier, the same time on a prior date, or from a prior time period when the heart rate corresponded to the present heart rate). As a further option, the past morphology may be a template created from a collection of patients or created from analytical modeling and tests. The template may be downloaded from an external programmer.

The programmable VCLAT-related parameters may also include AV association information, such as AV association thresholds. The AV association information includes the time intervals between P-wave events and the immediately successive R-wave events. The AV association information also includes the time intervals between successive R-wave events. The AV association information also includes the time intervals between R-wave events and the immediately successive P-wave events.

Each cardiac cycle includes an AS-VS interval which represents the time period between a P-wave and a successive R-wave. Cardiac cycles also include a VS-VS interval which represents the time period between successive R-waves. Each cardiac cycle also includes a VS-AS interval which represents the time period between an R-wave and a successive P-wave. The AS-VS, VS-AS and VS-VS intervals are assigned thresholds referred to as the AS-VS threshold, VS-AS threshold, and VS-VS threshold. The AS-VS, VS-AS and VS-VS thresholds collectively represent AV association thresholds. The AS-VS and VS-AS intervals change over time with the condition and health of the heart. The VS-AS intervals, VS-VS intervals and AS-VS intervals are used to identify changes in the AV association such as when an amount of change in the AS-VS, VS-AS and VS-VS intervals exceeds the corresponding VS-VS threshold, VS-AS threshold and AS-VS threshold. Optionally, the VS-VS threshold, the AS-VS threshold and the VS-AS threshold may be programmed (e.g., 50-1000 ms) in predetermined steps, such as 10 ms steps.

The VCLAT-related parameters may also include a flag indicating whether a morphology confirmation function is ON or OFF. When the morphology confirmation flag is ON, the method will compare current and past morphologies to distinguish between a potential accelerated junctional rhythm (AJR) and an accelerated idioventricular rhythm (AIVR). Other parameters include an overdrive pacing rate, an overdrive rate limit (e.g., min of (MSR or MTR), or a programmable rate), an overdrive AR interval limit (e.g., 100 ms-400 ms programmed in step of 10 ms), an overdrive rate delta (e.g., 1-10 ppm programmed in steps of 1 ppm, or rate dependent delta ppm), an overdrive scan count (e.g., 1-100 events), an overdrive time or count (e.g., 1-600 second), a diagnostics SEGM trigger, and a detection flag (e.g., On/Off), a conversion flag (e.g., On/Off).

Returning to FIG. 3, once the VCLAT related parameters are obtained at 302, next at 304, the method collects intracardiac (IC) signals. At 304, the IC signals are continuously recorded and the method calculates an atrial and ventricular event short history sequence such as over 10 to 100 events.

At 306, the method calculates AS-VS intervals and changes or deviations in the AS-VS interval between current and prior events. The method also calculates VS-VS intervals and VS-AS intervals and changes or deviations in the VS-VS interval and the VS-AS interval between current and prior events. The VS-VS, AS-VS and VS-AS intervals are used when the atrial event is an intrinsic event, as well as when the atrial event is a paced event. The VS-VS, AS-VS and VS-AS intervals may be between two individual successive cardiac cycles. Alternatively, the VS-VS, AS-VS and VS-AS intervals changes may be between i) an average, mean or median for a current set of cardiac cycles (e.g. 10) and ii) an average, mean or median for a past set of cardiac cycles. Optionally, the past VS-VS, AS-VS and VS-AS intervals may represent a running average, mean or median which is continuously updated by combining more recent cardiac cycles with much older cardiac cycles.

At 308, the method determines whether the change in the AS-VS interval exceeds the AS-VS threshold and whether the changes in the VS-VS interval and the VS-AS interval exceed the VS-VS and VS-AS thresholds. For example, the AS-VS interval may switch from 200 msec. to 60 msec. over one or a few beats, which is indicative of AJR. When the VS-VS, AS-VS and VS-AS intervals do not exceed the VS-VS, AS-VS and VS-AS thresholds, then flow returns to 304 along path 310. When one or more of the VS-VS threshold, AS-VS threshold and the VS-AS threshold is exceeded, this is determined to be an indication that the AV association has deviated sufficiently to indicate a potential VCLAT. In accordance with one embodiment, the method may declare an actual VCLAT based solely on the deviation of the VS-VS, AS-VS over the VS-VS, AS-VS and/or VS-AS interval threshold. In certain instances, there may be no intrinsic atrial event while atrial pacing is inhibited by the ventricular depolarization. When atrial pacing is inhibited and no intrinsic atrial event occurs, the AV association is changed as well. Alternatively, additional confirmation testing may be performed before a potential VCLAT is declared to be an actual VCLAT. Also, further testing may be performed to identify the type of VCLAT, namely AJR, AIVR or otherwise.

At 312, the method obtains the morphology pattern of a prior sinus rhythm, namely one that is normal. For example, the sinus rhythm may be obtained by the IMD under the control of a physician during programming or may be obtained by the IMD periodically, when the IMD determines that the patient is exhibiting normal sinus rhythm. Alternatively, the morphology pattern may be a prestored template.

At 314, the method obtains the current cardiac signal that is exhibiting the AV association that exceeded the AV threshold (s). The method analyzes the morphology of a current rhythm (or set of rhythms) with the morphology of a normal rhythm (or average of multiple normal rhythms). In general, AJR episodes exhibit a consistent morphology pattern in which the shape of the QRS complex remains relatively narrow and constant. The morphology of an AJR episode will resemble the morphology of a normal rhythm with a conducted sinus complex. The ventricular electrogram (VEGM) morphology of a junctional beat will be identical or very similar to that of a sinus (normal) conducted beat. However, the morphology of an AIVR episode differs from the VEGM morphology of the normal sinus conducted beat. In general, AIVR episodes exhibit an inconsistent morphology pattern, in which the shape of the QRS complex is wide and may vary between episodes or in some cases throughout an episode. The analysis at 314 may be through auto correlation, cross correlation and the like. Optionally, the analysis at 314 may be simpler, such as by comparing features of interest. For example, amplitudes of the P-wave, R-wave or T-wave may be compared from the current and past rhythms. Optionally, the elevation of the PQ segment and/or the ST segment may be compared from the current and normal rhythms. Optionally, time periods between the R-wave and T-wave may be compared form current and normal rhythms. Optionally, one or more of the PQ, ST or QRS complexes may be integrated to determine the area within the PQ, ST, QRS complexes and these areas compared between current and normal rhythms.

When the current and normal morphologies match, or morphology features of interest at least fall within predetermined limits of one another, flow moves along 316. An AJR is declared at 320 because the current morphology sufficiently matches the ventricular morphology associated with a normal (sinus) rhythm that had been previously stored in memory. When, at 314, the current and past morphologies do not match, or morphology features of interest fall outside of predetermined limits of one another, flow moves along 318. At 322, an AIVR is declared because the current morphology does not sufficiently match the normal morphology.

Next at 324, the method determines whether the episode exhibits a predetermined amount of regularity. At 326, the method determines whether a rate of the current cardiac signal exceeds an upper detection rate limit. For example, the upper detection rate limit may represent the lower limit of the first ventricular tachyarrhythmia (VT1) zone (e.g., 120 bpm). At 328, the method declares the potential VCLAT to be an actual VCLAT when one or both of the operations at 324 and 326 are true, namely i) the rate of the cardiac signal exceeds an upper detection rate limit and ii) the rhythm satisfies a rhythm regularity criteria. Optionally, one of the tests at either 324 or 326 may be omitted entirely and the other test relied upon entirely. At 328, various VCLAT event related information is stored in memory, such as the heart rate of the event, the event morphology, VS-VS interval, AS-VS interval, VS-AS interval, VS-VS change, AS-VS change, VS-AS change, and the like. In accordance with the above method, VCLAT rhythms are identified and confirmed, and AJR episodes are distinguished from AIVR episodes.

Figure 4:
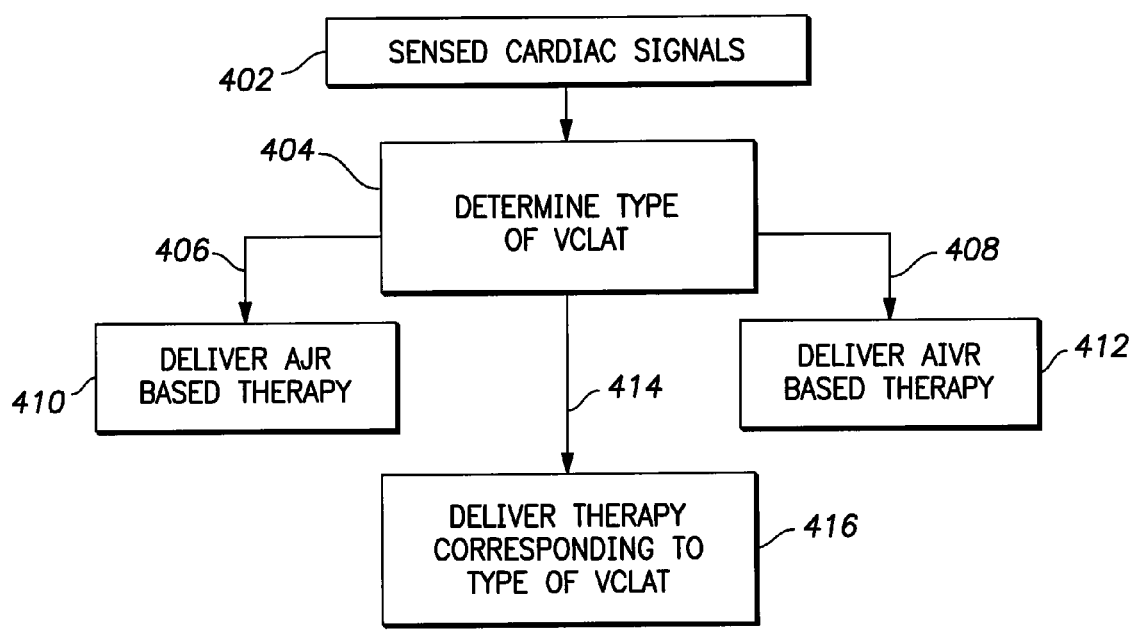
FIG. 4 illustrates a process for treating a transportless ventricular rhythm episode.

FIG. 4 illustrates a process for treating a transportless ventricular rhythm episode. At 402, the method begins by sensing cardiac signals similar to the manner discussed in connection with FIG. 3 from the heart. At 404, the method identifies the type of VCLAT that has occurred. For example, the type of VCLAT may be an accelerated junctional rhythm (AJR), an accelerated idioventricular rhythm (AIVR) or another type of VCLAT. When the method identifies an AJR, flow moves along 406 to deliver an AJR-based therapy at 410. When the method identifies an AIVR, flow moves along 408 to deliver an AIVR-based therapy at 412. When the method identifies another type of VCLAT, flow moves along 414. At 416, a therapy is delivered that corresponds to the type of VCLAT that has occurred. VCLAT episodes represent an intrinsic automaticity whereby particular tissues spontaneously discharge. As explained herein, embodiments are presented to treat VCLAT episodes by pacing tissue around foci at a rate that is faster than the intrinsic automaticity spontaneous discharge rate of the tissue causing the VCLAT episode. The therapies discussed herein are referred to as AJR-based therapies and AIVR-based therapies because it may be desirable to provide a different therapy based upon the type of VCLAT. When flow moves along 406, an AJR based therapy is delivered at 410. An aspect of AJR-based therapies is to introduce pacing pulses (e.g., overdrive pacing) in the atrium in order render the atrium refractory at select time periods during the cardiac cycle. When the atrial tissue is physiologically refractory, it will not respond to an atrial stimulus, regardless of the amplitude of the output pulse. It will also not respond to an APB or other intrinsic focus. Thus, while AJR derived tissue discharges may occur, the AJR derived discharge does not control the behavior (e.g., contraction timing) of the atrium. An AJR-based therapy seeks to suppress AJR atrial episodes and allow atrial conduction through normal pathways. There is also the situation with retrograde block, such that during an AJR event, there is also AV dissociation with the atrium still under the control of either sinus or an atrial paced rhythm but at a rate that is slower than the AJR. Increasing the atrial rate with pacing or pharmacologically to increase the sinus rate will often be conducted and suppress the AJR focus by a phenomenon known as overdrive pacing.

When flow moves along 408, AIVR-based therapy is delivered at 412. An aspect of AIVR-based therapies is to manage atrial activity to support ventricular contractions. AIVR episodes include an R-wave (ventricular depolarization) that is not preceded by a hemodynamically effective P-wave (atrial depolarization). Electrical depolarization of a cardiac chamber is usually followed by mechanical contraction of that same chamber. The AIVR-based therapy seeks to introduce a paced P-wave before the R-wave of an AIVR episode to improve hemodynamics by restoring atrial transport.

Figure 5:
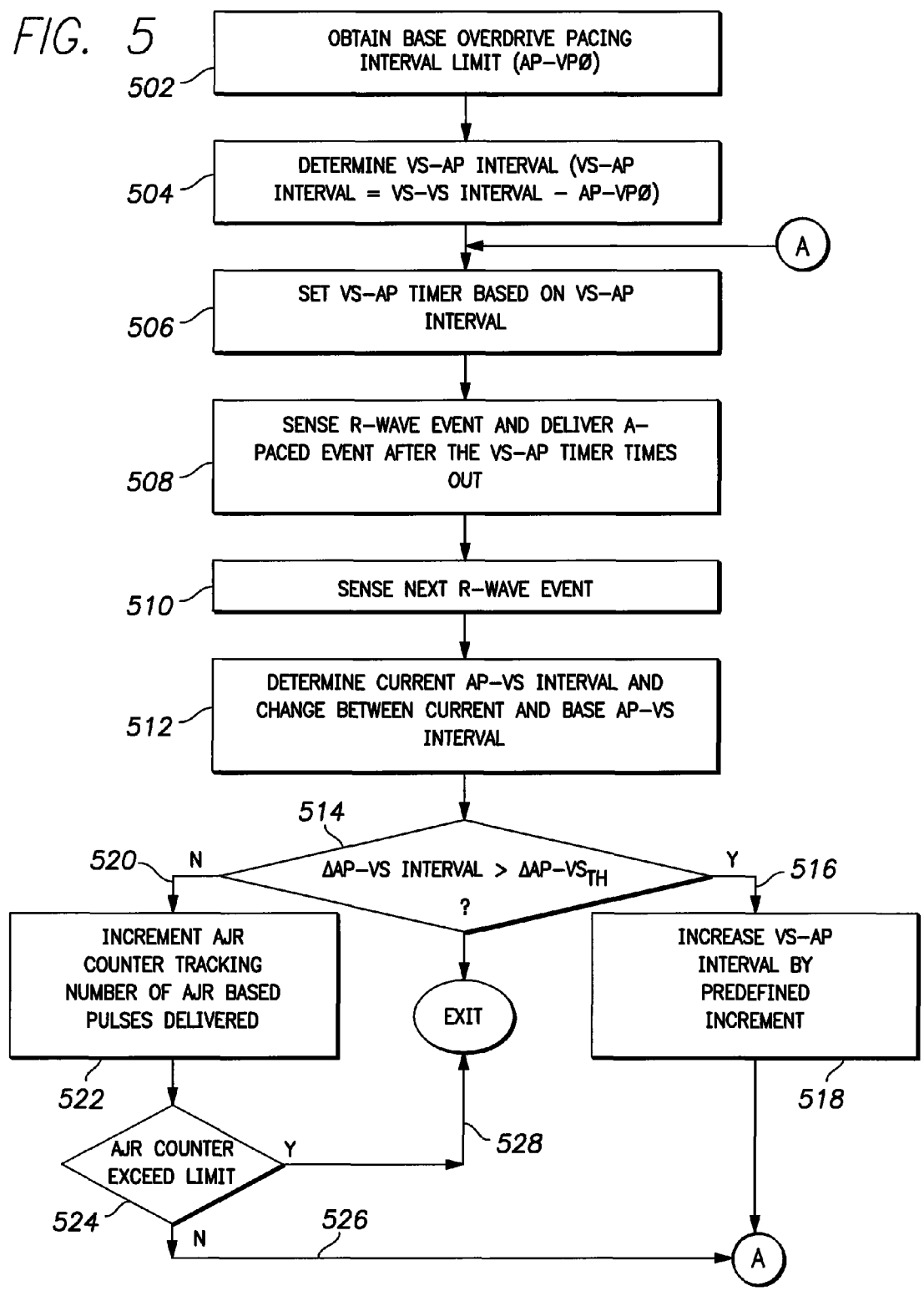
FIG. 5 illustrates a method for delivering an AJR based therapy.

FIG. 5 illustrates a method for delivering an AJR based therapy. At 502, a base overdrive AP-VP interval (AP-VPØ) limit is obtained, such as from historic data saved in memory. The base AP-VPØ limit represents an initial limit that may be used as the AP-VP interval between an atrial stimulus event and a subsequent ventricular stimulus. For example, the base AP-VPØ limit may be programmed to be between 100 ms and 400 ms. At 502, the VS-VS interval is determined from the measured cardiac signals. At 502, an AJR counter is also set to zero. At 504, the VS-AP interval is calculated as the difference between the VS-VS interval and the base AP-VPØ limit.

At 506, a VS-AP interval timer is set to the VS-AP interval calculated.

At 508, an R-wave event (ventricular contraction) is sensed (VS) and an atrial pacing pulse (A-paced event) (AP) is delivered after the VS-AP interval times out following the sensed R-wave event. Once the A-paced event is delivered, the method detects the next successive R-wave event at 510. At 512, a current AP-VS interval is measured between the A-paced event and the succeeding R-wave event detected at 510. A change ΔAP-VS interval is calculated between the current AP-VS interval measured at 512 and a prior AP-VS interval. The prior AP-VS interval may be the base AP-VSØ limit or a subsequent updated AP-VS interval.

At 514, it is determined whether the measured change in AP-VS interval (ΔAP-VS interval) exceeds a predefined change AP-VS interval threshold ($\Delta AP\text{-}VS_{TH}$). When the measure change in AP-VS interval exceeds the threshold, $\Delta AP\text{-}VS_{TH}$, this is an indication that the AJR episode may have been converted to a non-AJR episode by one or more pacing pulses delivered at 508 during one or more prior iterations. When ΔAP-VS interval>$\Delta AP\text{-}VS_{TH}$, flow moves along 516 where the process enters an iterative recovery pacing scheme. The recovery pacing scheme repeats the operations at 506 to 518 multiple times with the VS-AP interval being incrementally increased during each iteration. For example, the operations at 506 to 508 may be repeated 3, 5 or more iterations, at each of which the VS-AP interval is progressively increased such as from 50 msec. to 100 msec. to 150 msec. and the like. The operations at 506 to 518 are repeated, so long as the change in the AP-VS interval (ΔAP-VS interval) exceeds the threshold, until reaching an intended pacing rate. The recovery pacing scheme at 506 to 518 gradually increases the AS-AP interval until the pacing rate reaches a programmed or otherwise intended pacing rate (e.g., the base rate). Alternatively, an atrial intrinsic event may occur before the next A-paced event is delivered. The both of the scenarios, the system complete the therapy and exit.

Returning to 514, when the AP-VS interval change ΔAP-VS interval is less than or equal to the threshold ΔAP-VS interval$_{TH}$, flow moves along 520. At 522, a counter is incremented to track the number of AJR based overdrive pacing pulses delivered in connection with a current AJR episode. At 524, it is determined whether the AJR counter exceeds a limit representing a number of predefined pacing events without the AJR rhythm ceasing or being converted to a normal rhythm. When the AJR counter is below the limit, flow moves along 526 to return to point A at 506. When flow moves from 524 to 506, the VS-AP interval remains unchanged from the prior iteration. At 508, the next R-wave is sensed and the A-pacing pulse is delivered the VS-AP interval thereafter. At 510, the next R-wave event is sensed, and the determination and test at 512 and 514 are repeated. When the AJR counter exceeds the limit at 524, flow moves along 528 to exit the process of FIG. 5. Otherwise, it will be logged as a non-converted episode and operation returns to point A. The test at 524 manages overdrive pacing to be repeated up to a programmed number of times when an AJR rhythm does not convert. The test at 524 may be used to prevent overdrive pacing indefinitely for an unconverted, persistent AJR rhythm. It is highly unlikely that an AJR will not be converted however it may only be suppressed and when the period of rapid pacing slows in accord with the algorithm, the AJR may again be present. If recognized again, the algorithm may allow for an increase in paced rate. Each time the algorithm has to increase its paced rate to overdrive suppress the AJR, it may remain at the higher rate for progressively longer periods of time. Further, if while there is atrial pacing at the higher rate, the junctional focus accelerates further and again usurps control from the overdrive pacing, the AJR algorithm should allow for a further increase in atrial paced rate only limited by an independently programmable maximum paced rate, the maximum tracking rate and/or the maximum sensor rate.

Atrial pulses may fail to capture because, among other things, of retrograde conduction. For example, an atrial pulse may not capture when the heart is exhibiting a rhythm generally referred to as repetitive non-reentrant ventriculo-atrial synchrony. Optionally, the AJR based and/or AIVR based therapies delivered in accordance with embodiments herein may include an atrial capture confirmation process, such as described in U.S. Pat. Nos. 6,477,419, 6,498,949 and 6,493, 583, all of which are expressly incorporated herein by reference in their entireties. Atrial capture confirmation may be activated to determine whether atrial pacing is effective. When a lack of atrial capture is confirmed for a predetermine number of cardiac cycles (e.g., two consecutive cycles), the therapy may be modified by shortening the interval between an atrial paced event (AP) and the subsequent ventricular sensed event (VS) (e.g., the AP-VS interval). The AP-VS interval may be a programmable interval, such as 50 ms, and held at this programmed interval for a predetermined number of cardiac cycles (e.g., three or more). By shortening the AP-VS interval, the method provides the atrium with more time to physiologically recover following the occurrence of an intrinsic P-wave. With successful atrial capture, shortening the AP-VS interval should at least prevent retrograde conduction following subsequent ventricular sensed events. Once capture is confirmed, the AP-VS interval may be restored to its previously programmed value and the atrial capture confirmation process reinitiated to validate capture. Once capture is validated, the flow exits FIG. 5, such as 514.

Figure 6:
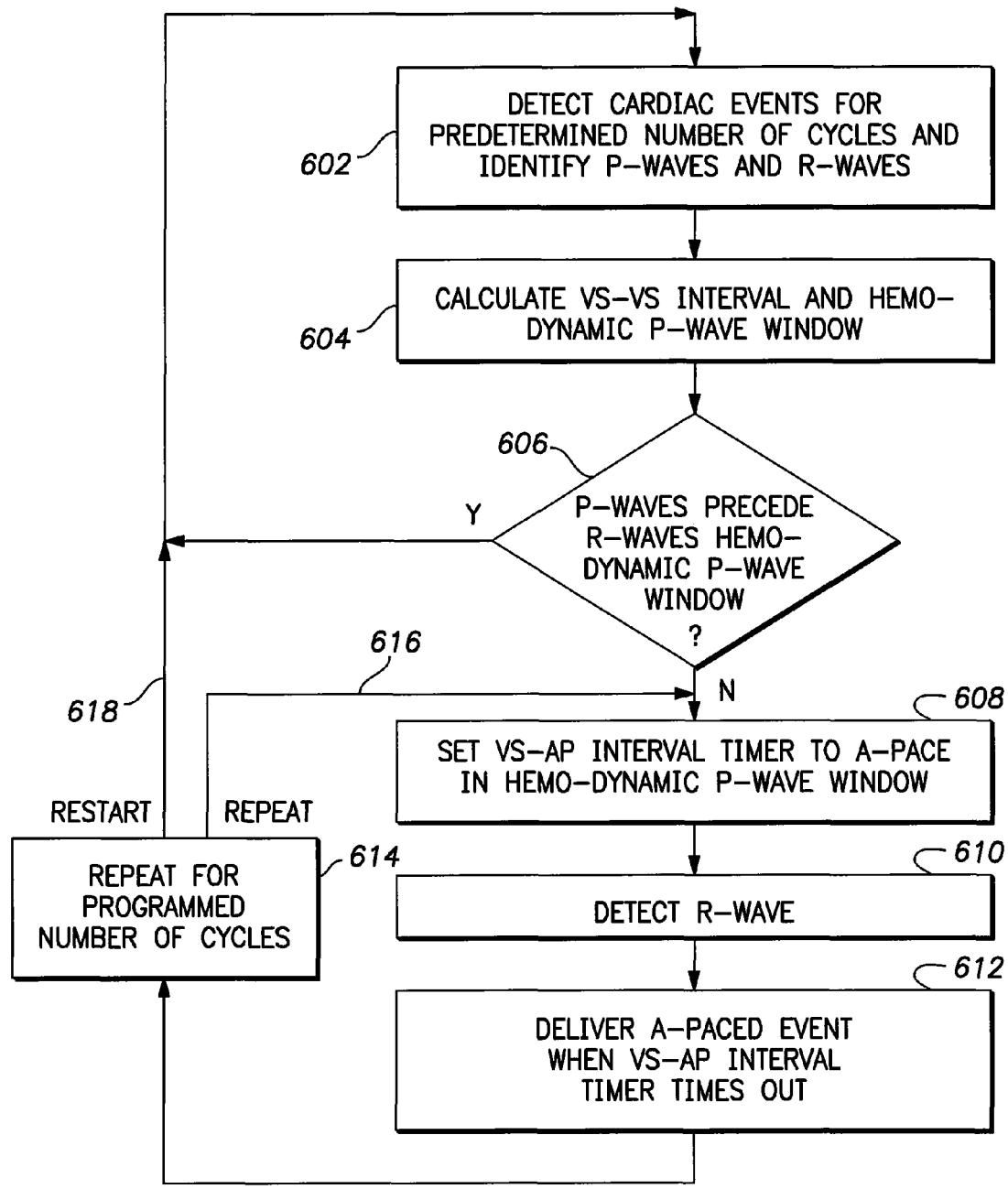
FIG. 6 illustrates a method for delivering an AIVR based therapy.

FIG. 6 illustrates a method for delivering an AIVR based therapy. Beginning at 602, the IMD detects cardiac events for a predetermined number of cardiac cycles (e.g., 2, 5, 10, etc). At 602, the method identifies P-waves (if any) within the detected cardiac cycles and R-waves within the cardiac cycles. Not every cardiac cycle will include a P-wave. Further, certain cardiac cycles may exhibit P-waves and R-waves, yet the interval between the P-wave and an associated R-wave may be unduly short such that poor hemodynamic performance occurs. The very short interval would also reflect that the two events are coincidental and that the atrial depolarization does not conduct to the ventricle to cause the ventricular depolarization.

At 604, the method calculates the VS-VS interval associated with the cardiac cycles, as well as a hemodynamic P-wave window. The hemodynamic P-wave window represents a time interval that precedes each R-wave, in which a P-wave should occur in order to provide hemodynamic support for the ventricular contraction caused by the subsequent R-wave. When an AIVR episode occurs, generally R-waves are not preceded by P-waves at all or within the proper hemodynamic P-wave window. Often, an AIVR episode may occur without any P-waves. Alternatively, the P-waves may exist, but be sufficiently out of synchronization to not provide hemodynamic support for the subsequent ventricular contraction (R-waves).

At 606, the method of FIG. 6 determines whether P-waves exist within the hemodynamic P-wave windows that precede associated R-waves. Optionally, 606 may be omitted because P-waves will generally not exist within this hemodynamic P-wave window when an AIVR episode occurs. When a P-wave is absent, flow moves to 608 where a VS-AP interval timer is set. Once the timer is set at 608, flow moves to 610 where the next R-wave is detected and the VS-AP interval timer is started. At 612, an A-paced event is delivered when the VS-AP interval timer times out following the previously detected R-wave. The operations at 608-612 introduce atrial events (albeit paced) preceding R-waves by a time period that is timed to support the hemodynamics of the ventricular contractions.

Next, flow moves to 614 where it is determined whether the A-paced events have been introduced for a predetermined programmed number of cycles. If the A-paced events have been utilized for less than the programmed number of cycles, flow returns along 616 to 608 where the VS-AP interval timer is reset. Then, at 610 and 612, the next R-wave is detected and an A-paced event is delivered when the VS-AP interval timer again times out. The process repeats until the programmed number of cardiac cycles set at 614 are paced with A-paced events. Once the programmed number of cycles has been reached at 614, flow moves along 618 to return to the beginning of the method at 602. Optionally, the AIVR based therapy may be terminated when flow moves from 614 along 618, or when sensed P-waves are determined at 606 to occur within the hemodynamic P-wave window.

Figure 7:
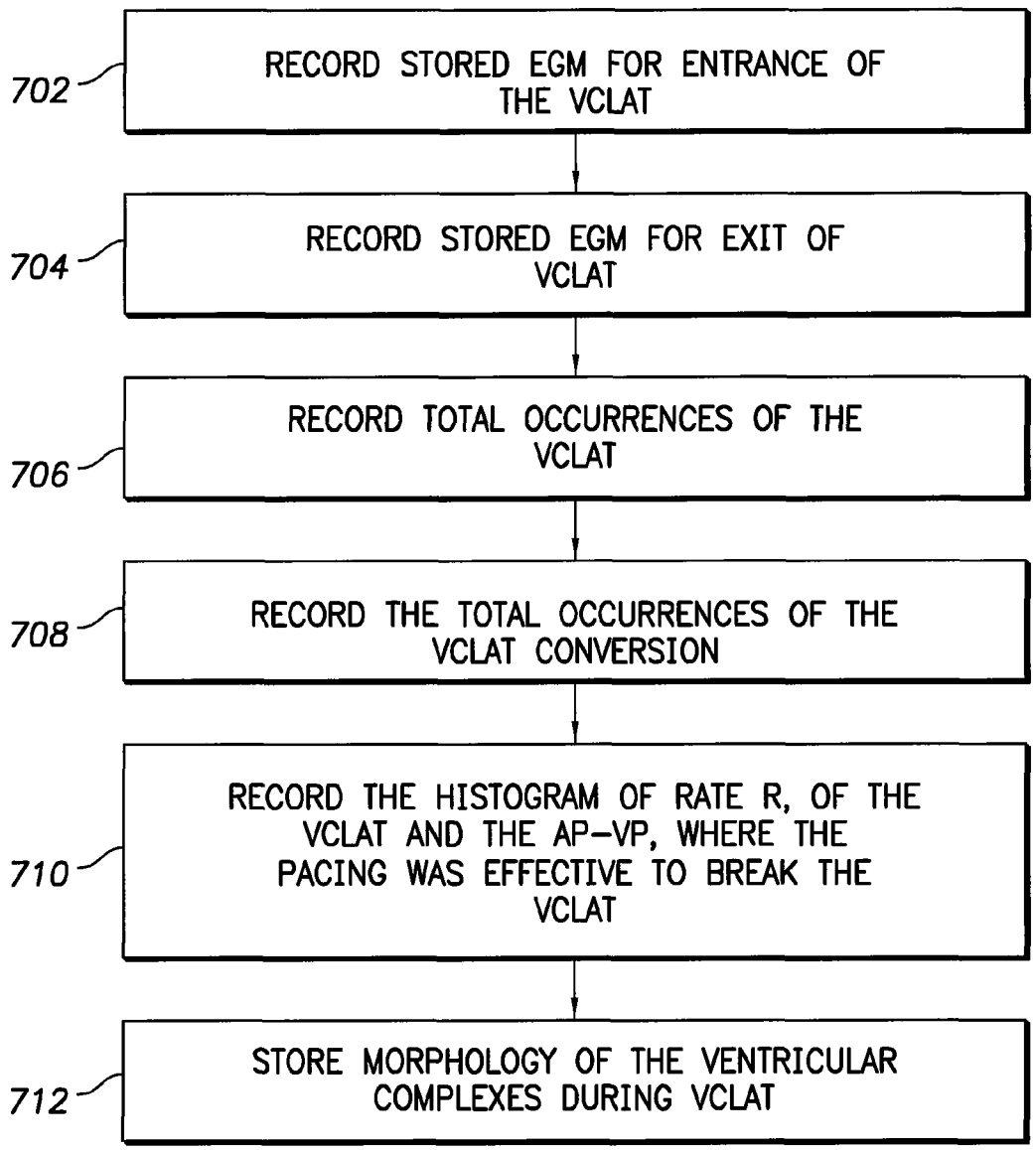
FIG. 7 illustrates a diagnostic data collection process performed in accordance with an embodiment.

FIG. 7 illustrates a process for collecting diagnostic data during and after VCLAT episodes. Beginning at 702, the method records the stored intracardiac electro-cardiogram (SEGM) for the cardiac signals at the time when the VCLAT initiated, also referred to as the entrance of the VCLAT. At 704, the method records the SEGM for the cardiac signal at the time when the VCLAT ceased, also referred to as exit of the VCLAT.

At 706, the method records the total occurrences of the VCLAT. For example, a VCLAT episode may include 5, 10 or more cardiac cycles that exhibit an AJR rhythm or an AIVR rhythm. Multiple VCLAT episodes may occur over a day, week, month or year. Thus, the total number of the occurrences of the AJR or AIVR events in an episode and the total number of VCLAT episodes over a period of time are recorded. At 708, the method records the total occurrences of when the VCLAT episode was converted back to a normal sinus rhythm with a therapy or through self termination. For example, over the course a day, a week, a month and the like, a patient may experience several VCLAT episodes (which are recorded at 706). All or only a portion of these VCLAT episodes may be converted back to normal sinus rhythm through the AJR based therapy or AIVR based therapy delivered by the IMD. At 708, the method records the total number occurrences of the VCLAT rhythm that were converted back to a normal sinus rhythm through some type of VCLAT based therapy. At 706, the method may also record the type of VCLAT based therapy and the number of times such therapy was applied before conversion back to a normal sinus rhythm was successful.

At 710, the method records a histogram of the heart rate Ri of the cardiac signal during the VCLAT episode. At 710, the method also records the AR interval (ARi) where the VCLAT therapy was effective in breaking or converting the VCLAT rhythm back to a normal sinus rhythm. At 712, the method stores the morphology of the ventricular complexes during the VCLAT episode. By storing the morphology, the method supports a diagnosis of different rhythms, such as AJR rhythms and AIVR rhythms. The method also records a stored electrogram associated with entry to and/or exit from a VCLAT episode to allow the clinician to determine if the algorithm correctly analyzed the rhythm and intervened successfully.

FIGS. 8-13 illustrate examples of normal and VCLAT rhythms that are detected and treated in connection with embodiments of the present invention. In VCLAT episodes, although a sensed R wave may be preceded by a paced or sensed atrial event, the interval from the atrial paced or atrial sensed event to the ventricular sensed event (AP-VS or AS-VS) is too short thereby identifying the R wave as an accelerated event or transportless ventricular rhythm. If the QRS morphology is stable, narrow and consistent with morphology template that is stored in the device memory, it is an accelerated junctional complex.

Figure 8:
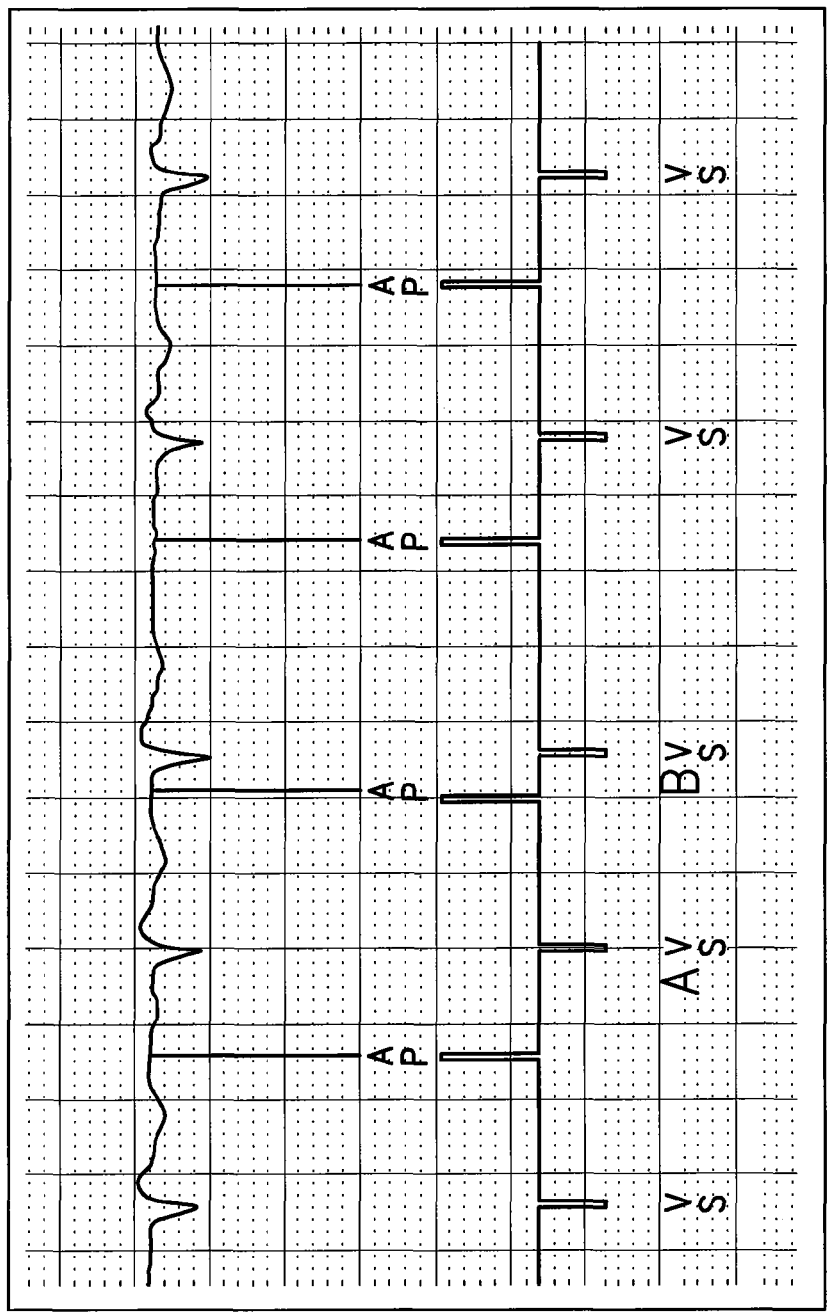
FIG. 8 illustrates an example of a VCLAT rhythm.

FIG. 8 illustrates a surface ECG signal detected over time, with markers to denote atrial paced events (AP) and ventricular sensed events (VS). The event at point A corresponds to a normal atrial paced rhythm with intact atrioventricular nodal conduction with an AP-VS interval of approximately 200 msec. The event at point B corresponds to an abnormal VCLAT cycle with an AP-VS interval of approximately 60 msec. from AP to VS. The interval B is too short with respect to physiologic conduction. Hence, the VS component of the AP-VS is not conducted from the atrial stimulus, but instead is an accelerated junctional complex in that the morphology of the QRS is identical to the conducted complex.

Figure 9:
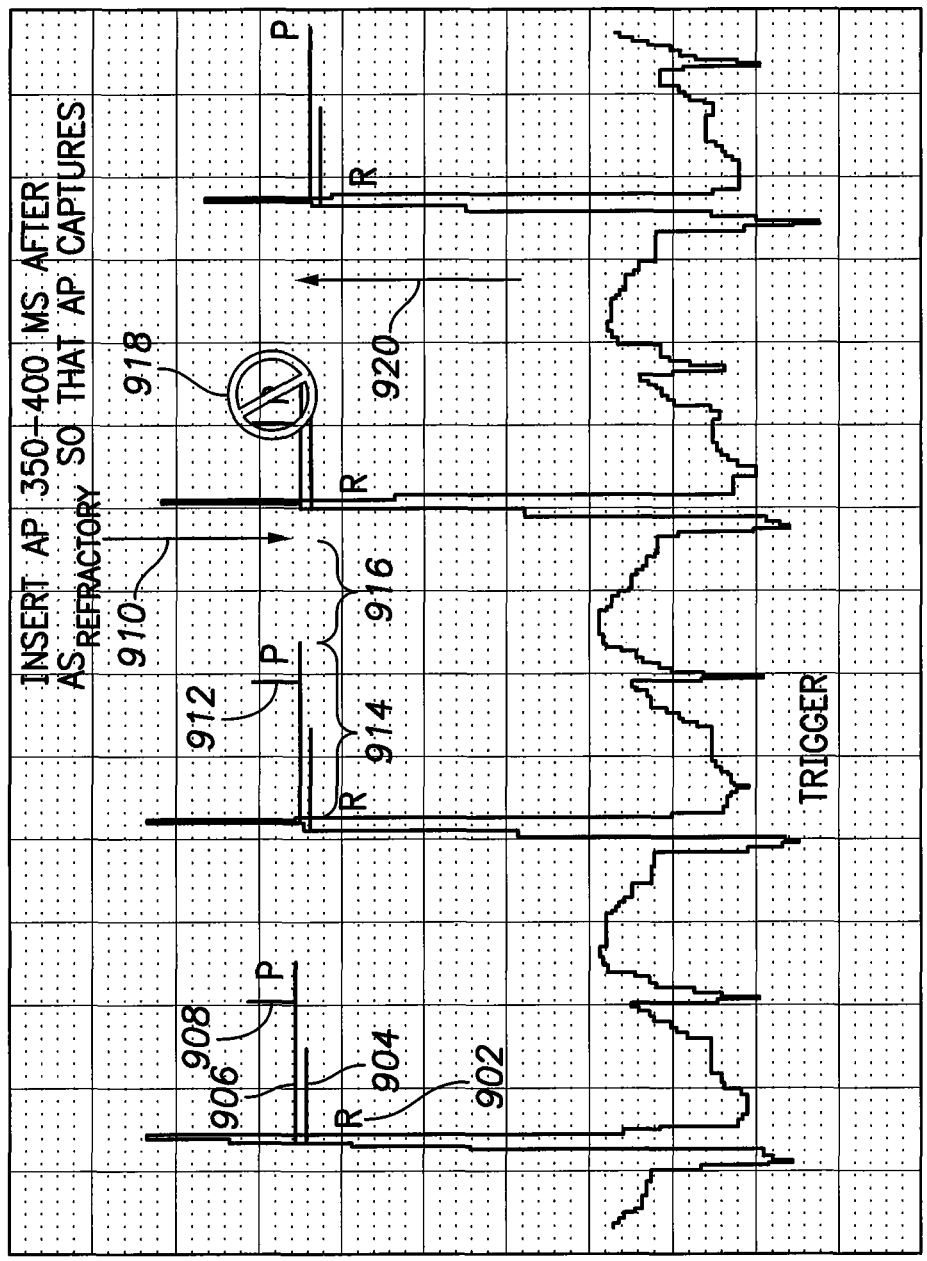
FIG. 9 illustrates an example of an accelerated junctional rhythm.

FIG. 9 illustrates an example of first degree AV block that would be labeled as an accelerated junctional rhythm. FIG. 9 illustrates an R-wave at 902, a ventricular refractory period 904, a post ventricular atrial refractory period (PVARP) 906 and a P wave 908. The P-wave 908 occurs during the PVARP 906. The arrhythmia of FIG. 9 represents a slow rate, apparent loss of atrial transport because of first degree AV block. To manage the arrhythmia illustrated in FIG. 9, the embodiments described herein would deliver an atrial pacing stimulus (AP) at a predetermined time following the sensed atrial event (AS). A first A-pacing stimulus may not be effective to restore normal hemodynamics because the resultant AP-VS interval may be too short. However, inserting an A-pacing stimulus will prevent retrograde conduction from occurring and restore AV synchrony.

The A-pacing stimulus (AP) is inserted at the point denoted at 910 which follows the PVARP 914 by a programmed amount 916 (e.g., 300-450 msec.) depending on the rate of the accelerated rhythm. The A-pacing stimulus AP occurs even though an atrial sensed event 912 occurred immediately before. The AP 910 renders the atrium and AV node physiologically refractory to prevent retrograde conduction. If a stable VS or VP is followed by an AS complex at a stable V-AS interval, the AP stimulus is delivered progressively closer and even coinciding with the VS or VP event. When atrial capture occurs, a potential intrinsic atrial event 918 is prevented, where but for the AP 910, an intrinsic atrial event 918 might otherwise occur. Additional A-pacing stimulus 920 may be delivered at a time when the atrium is no longer refractory. This will allow for atrial capture but will also render the atrial and AV nodal tissue physiologically refractory so that it cannot conduct retrograde. The next AP occurs at an accelerated rate (overdrive) and thereafter the atrial tissue and AV nodal tissue are recovered and can capture and conduct. As such, the rate is accelerated slightly and AV synchrony is restored. After a period of overdrive pacing (similar to St. Jude Medical's AF Suppression algorithm), the atrial paced rate will begin to slow. If AJR promptly (within a programmable time limit or number of cycles of intrinsic heart rhythm) recurs, the above algorithm is repeated but with overdrive pacing sustained for progressively longer periods of time.

Figure 10:
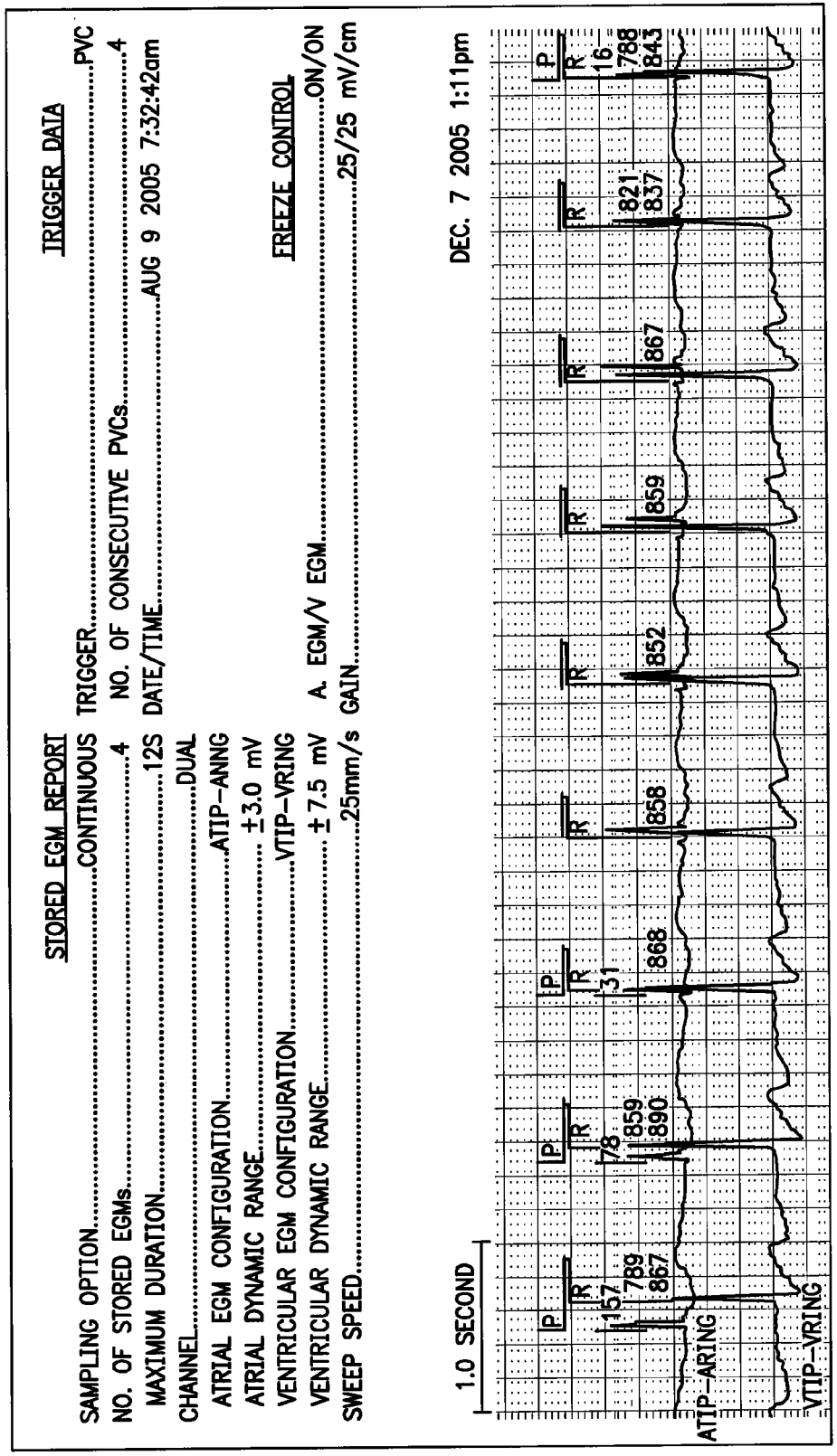
FIG. 10 illustrates an example in which the PR interval is too short to be hemodynamically effective.

FIG. 10 illustrates another example, in which a P-wave occurs prior to each QRS complex which has a stable normal morphology. The AS-VS interval is too short to have been effective and some time the P-wave is not detectable as they are buried in the R-wave, and hence, this rhythm is an accelerated junctional rhythm. In this situation, the methods and systems start delivering atrial stimulus at a slightly accelerated rate that will take over and drive the atrium with intrinsic conduction.

Figure 11:
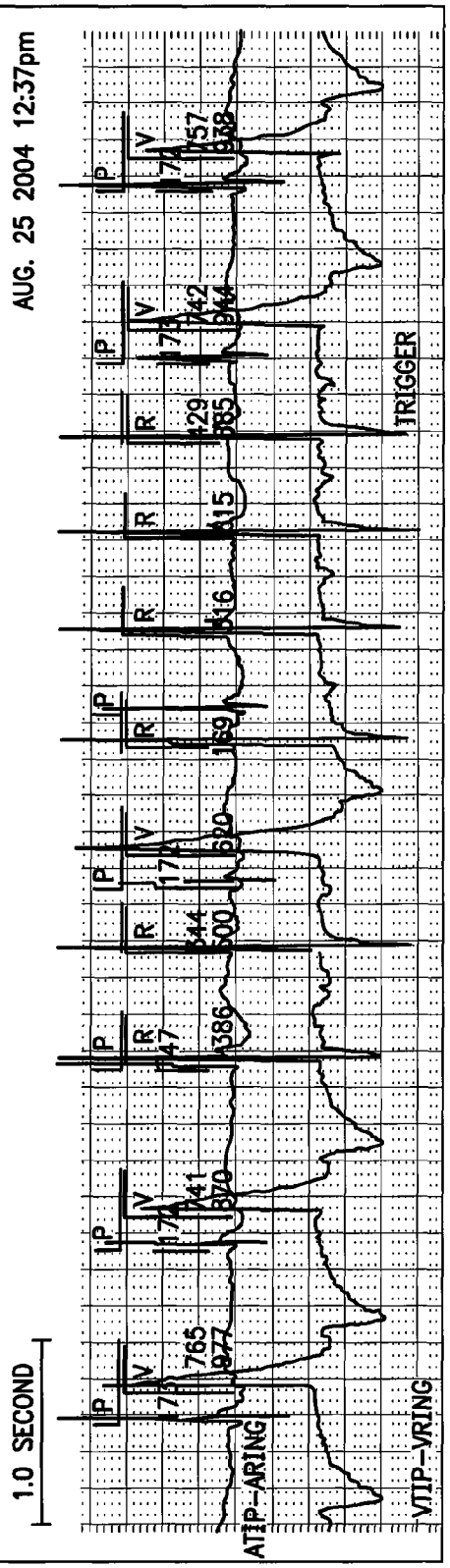
FIG. 11 illustrates an example of an accelerated idioventricular rhythm occurs.

FIG. 11 illustrates another example in which an accelerated idioventricular rhythm occurs. The AIVR is too short to be sustained. Depending on the number of cycles programmed into the IMD for AIVR detection, the IMD may or may not trigger an atrial output.

Figure 12:
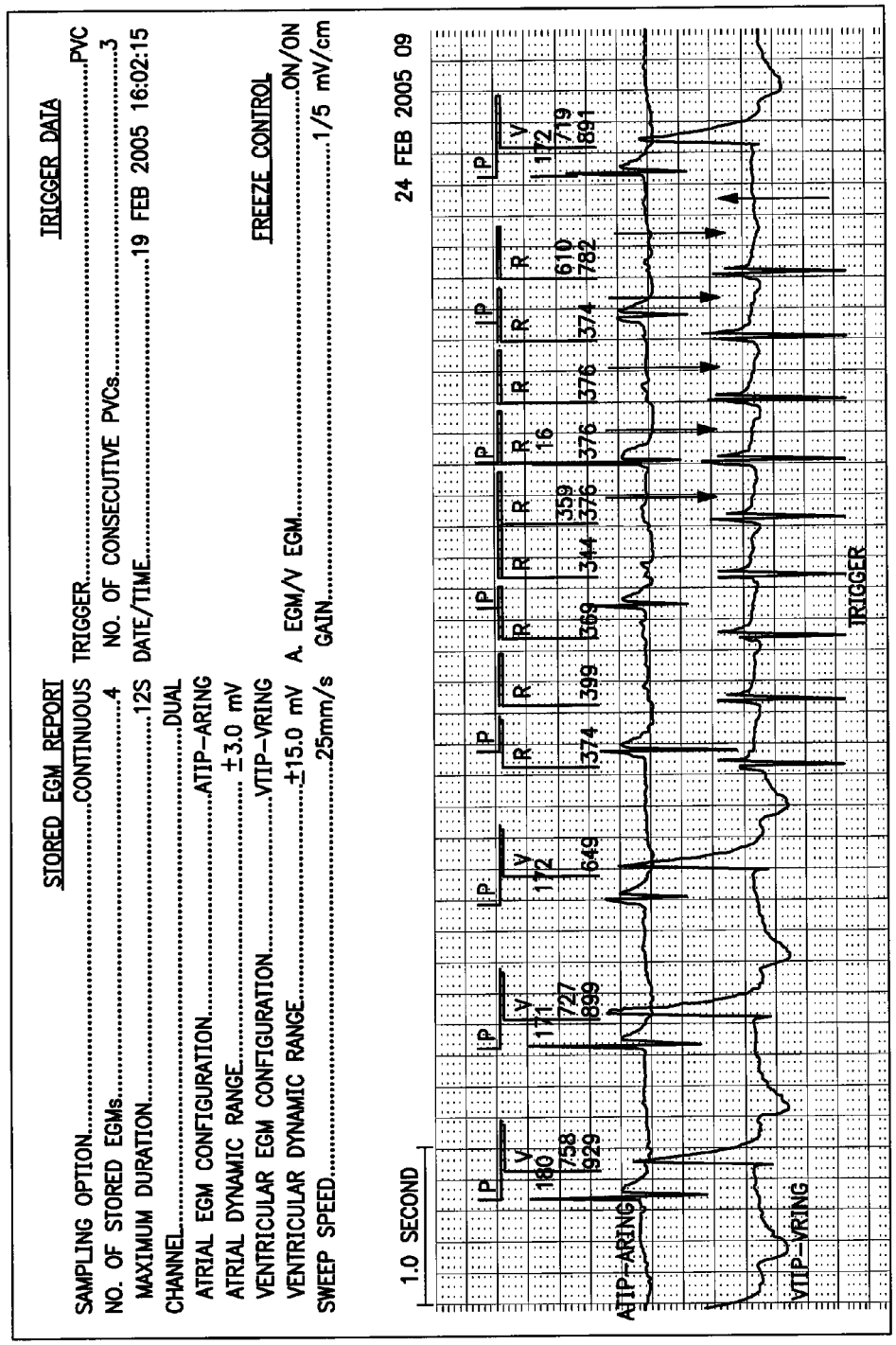
FIG. 12 illustrates an example of a ventricular tachycardia.

FIG. 12 illustrates a ventricular tachycardia (VT) such as when the heart rate is above a programmed lower VT limit (e.g., 170 bpm). This would be above any upper rate limit (150 bpm) to preclude delivery of an atrial stimulus. If the atrium were overdriven, the IMD could coincidentally insert an atrial stimulus before the native QRS complex is detected by the ventricular sensing circuit of the pulse generator. By inserting an atrial stimulus before a native QRS complex, this would help to improve atrial transport. The downward directed arrows represent atrial stimuli inserted after "n" cycles to recognize the rhythm and a lack of a consistent AS-VS interval. The sequence ends with ventricular pacing (VP) at the upward arrow if ventricular capture is confirmed. The delivery of VP (upward arrow) ends the algorithm.

Figure 13:
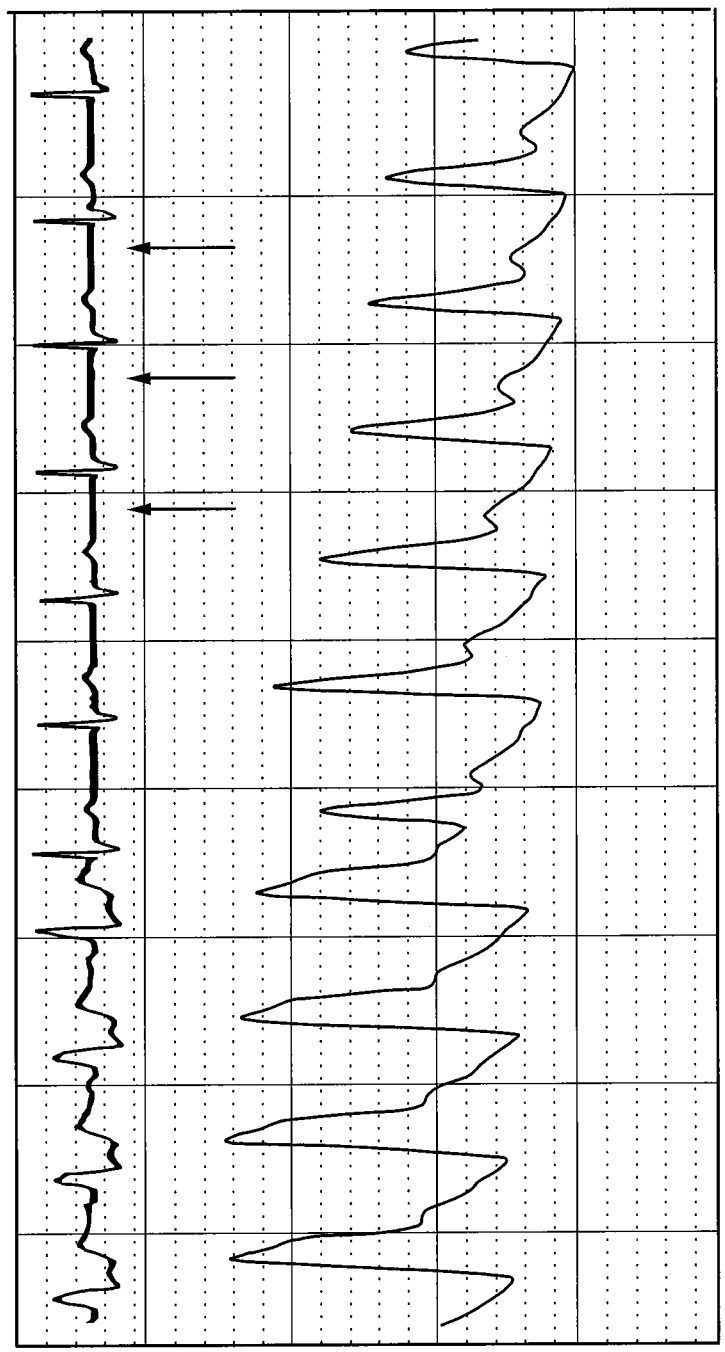
FIG. 13 illustrates an example of an accelerated idioventricular rhythm with a marked drop in blood pressure.

FIG. 13 illustrates an accelerated idioventricular rhythm with a marked drop in blood pressure (BP) and shortening of the systolic ejection period with adverse hemodynamic consequences. In accordance with an embodiment (e.g., the method of FIG. 6), atrial paced events are placed before each "narrow" QRS complex (as denoted by the upward directed arrows). The atrial paced events may help to restore hemodynamics since the rates are virtually identical for sinus rhythm and the AIVR rhythm illustrated in FIG. 13.

Figure 2:
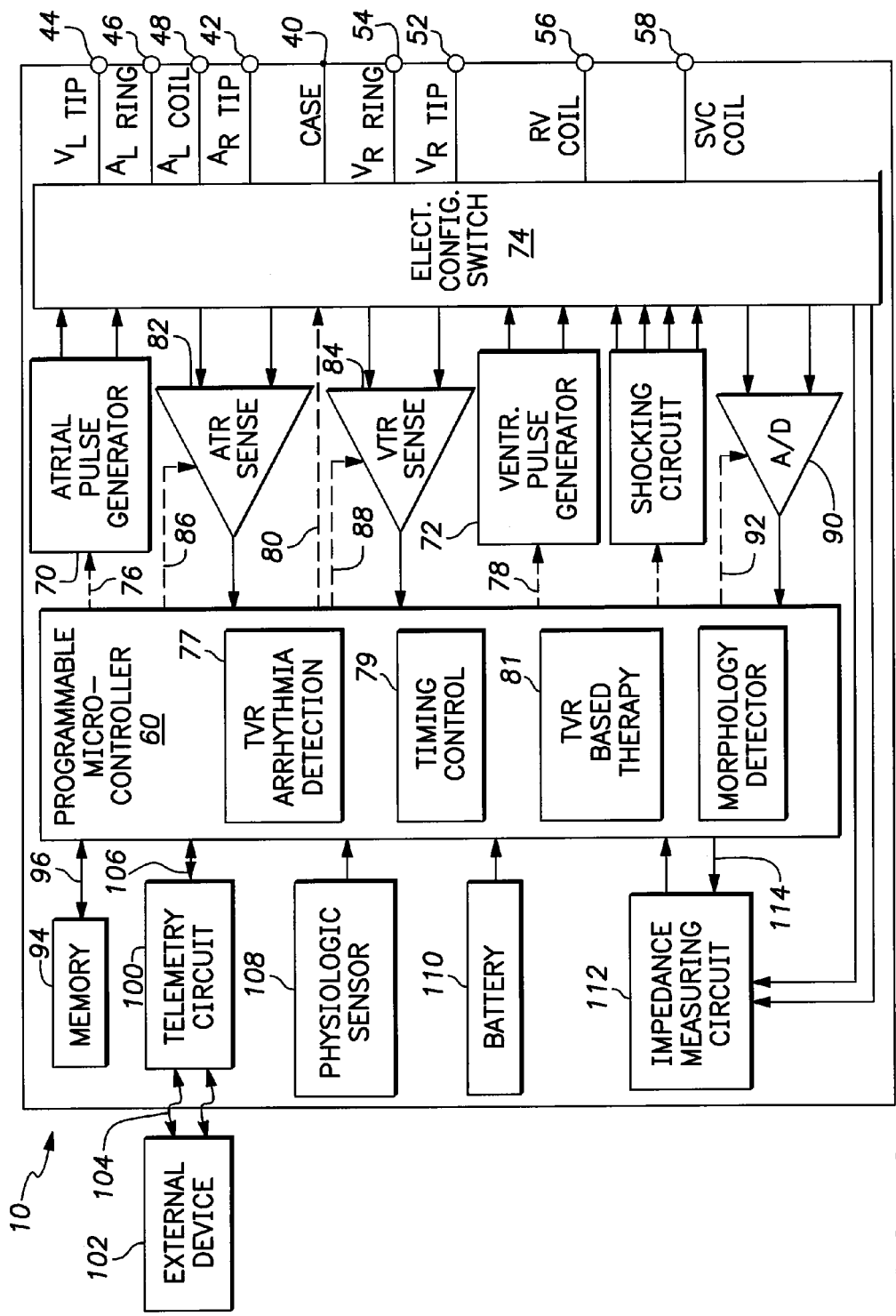
FIG. 2 illustrates a simplified block diagram of the multi-chamber implantable stimulation device.

As illustrated in FIG. 2, a simplified block diagram is shown of the multi-chamber implantable stimulation device 10, which is capable of treating both fast and slow arrhythmias including VCLAT rhythms with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial tip electrode 22.

To achieve left chamber sensing, pacing and shocking, the connector includes at least a left ventricular tip terminal 44, a left atrial ring terminal 46, and a left atrial shocking terminal 48, which are adapted for connection to the left ventricular tip electrode 26, the left atrial tip electrode 27, and the left atrial coil electrode 28, respectively.

To support right chamber sensing, pacing and shocking, the connector further includes a right ventricular tip terminal 52, a right ventricular ring terminal 54, a right ventricular shocking terminal 56, and an SVC shocking terminal 58, which are adapted for connection to the right ventricular tip electrode 32, right ventricular ring electrode, 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals including relative post-ventricular atrial refractory period (RPVARP) intervals, noise detection windows, evoked response windows, alert intervals, marker channel timing, etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74 for detecting the presence of cardiac activity in each of the four chambers of the heart. Accordingly, the atrial and ventricular sensing circuits, 82 and 84, may include dedicated sense amplifiers, multiplexed amplifiers, or shared amplifiers. The switch bank 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, respectively, in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the microcontroller 60 of device 10 provides VCLAT arrhythmia detection module 77 which utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

The VCLAT arrhythmia detection module 77 further detects transportless ventricular rhythms (VCLAT) and collects diagnostic data as described throughout. Examples of VCLAT detection and data collection processes are described in connection with FIGS. 3, 7 and 8-13. Such a rhythm may be detected when a predetermined number of, for example, ten, successive R-waves are detected at a rate below a programmed given rate but above a base rate, wherein each successive R-wave fails to be preceded by a P-wave or atrial pacing. In this event, atrial transport is deemed to be lost at a rate above a base rate and VCLAT therapy is initiated as described subsequently. The programmed given rate above the base rate may be, for example, 100 beats per minute (bpm) and the base rate may be, for example, 60 bpm. A VCLAT based therapy module 81 delivers various therapies as described throughout (e.g., the AJR based therapy of FIG. 5, and the AIVR based therapy of FIG. 6). FIGS. 8-13 illustrate further examples of VCLAT based therapies.

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 employs lithium/silver vanadium oxide batteries, as is true for most (if not all) such devices to date.

As further shown in FIG. 2, the device 10 is shown as having an impedance measuring circuit 112 which is enabled by the microcontroller 60 by a control signal 114. The impedance measuring circuit 112 is not critical to the present invention and is shown for only completeness.

To provide the function of an implantable cardioverter/defibrillator (ICD) the device must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high energy (11 to 40 Joules), as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

The flow charts describe an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. An implantable medical device for detecting a ventricular complex with loss of atrial transport of a heart lacking atrial transport, comprising:
   a housing;
   sensor inputs configured to receive cardiac signals from a heart;
   a sensing module to sense cardiac signals representative of a rhythm originating from the heart;
   a rhythm detection module to determine a change in AV association and to identify a potential ventricular complex with a loss of atrial transport (VCLAT) based on the change in AV association;
   wherein the rhythm detection module distinguishes the type of potential VCLAT as a potential accelerated junctional rhythm (AJR) and a potential accelerated idioventricular rhythm (AIVR).

2. The device of claim 1, wherein the rhythm detection module identifies the potential VCLAT when the change in AV association exceeds an AV association threshold.

3. The device of claim 1, wherein the AV association threshold represents at least one of an VS-VS interval threshold and a AS-VS interval threshold, the rhythm detection module to monitor at least one of VS-VS intervals and AS-VS intervals from the cardiac signals, the rhythm detection module identifying the change in the AV association when an amount of change in the at least one of VS-VS intervals and AS-VS intervals exceeds the corresponding VS-VS interval threshold and AS-VS interval threshold.

4. The device of claim 1, further comprising a morphology detector module to compare a current morphology of a current rhythm with a stored template documenting the morphology of the normal rhythm, and to declare the current rhythm to be an accelerated junctional rhythm when the current morphology matches the morphology of the normal rhythm.

5. The device of claim 1, further comprising a morphology detector module to compare current and past morphologies of current and past rhythms, respectively, the morphology module to declare the current rhythm to be an accelerated idioventricular rhythm when the current morphology does not match the past morphology of the rhythm identified as normal with a patient's usual ventricular activation pattern.

6. The device of claim 1, wherein the rhythm detection module determines when a rate of the cardiac ventricular rhythm exceeds a detection rate limit, and when the rate is faster than a detected atrial rate and declares the potential VCLAT to be an actual VCLAT based thereon.

7. The device of claim 1, wherein the rhythm detection module determines a rhythm regularity and declares the potential VCLAT to be an actual VCLAT when the rhythm regularity satisfies a regularity criteria.

8. The device of claim 1, wherein the rhythm detection module declare the potential VCLAT to be an actual VCLAT when a rate of the cardiac signal exceeds an upper detection rate limit and when the rhythm satisfies a rhythm regularity criteria.

9. The device of claim 1, further comprising memory to store a rate of the rhythm when the potential VCLAT is declared to be an actual VCLAT.

10. The device of claim 1, further comprising memory to store the electrogram (either atrial, ventricular, composite or multiple simultaneous intracardiac leads) when the potential VCLAT is declared to be an actual VCLAT.

11. The device of claim 1, wherein the rhythm detection module declares the potential VCLAT is a potential AIVR when current and past morphology patterns essentially differ, and wherein the rhythm detection module declares the potential VCLAT is a potential AJR when current and past morphology patterns are essentially similar.

12. A method for detecting a ventricular complex with loss of atrial transport of a heart, comprising:

sensing cardiac signals representative of a rhythm originating from the heart;
  determining a change in AV association;
  identifying a potential ventricular complex with loss of atrial transport (VCLAT) based on the change in AV association; and
  distinguishing the type of potential VCLAT as a potential accelerated junctional rhythm (AJR) and a potential accelerated idioventricular rhythm (AIVR).

13. The method of claim 12, further comprising determining when the change in AV association exceeds an AV association threshold; and identifying the potential VCLAT when the change in AV association exceeds an AV association threshold.

14. The method of claim 12, wherein the AV association threshold represents at least one of an VS-VS interval threshold and a AS-VS interval threshold, the method further comprising monitoring at least one of VS-VS intervals and AS-VS intervals from the cardiac signals, and identifying the change in the AV association when an amount of change in the at least one of VS-VS intervals and AS-VS intervals exceeds the corresponding VS-VS interval threshold and AS-VS interval threshold.

15. The method of claim 12, further comprising comparing a current morphology of a current rhythm with a past morphology of a past rhythm, and declaring the current rhythm to be an accelerated junctional rhythm when the current morphology matches the past morphology of the past rhythm.

16. The method of claim 12, further comprising comparing a current morphology of a current rhythm with a past morphology of a past rhythm, and declaring the current rhythm to be an accelerated idioventricular rhythm when the current morphology does not match the past morphology of the past rhythm.

17. The method of claim 12, further comprising determining when a rate of the cardiac signal exceeds an upper detection rate limit.

18. The method of claim 12, further comprising determining a rhythm regularity and declaring the potential VCLAT to be an actual VCLAT when the rhythm regularity satisfies a regularity criteria.

19. The method of claim 12, wherein the potential VCLAT is declared a potential AIVR when current and past morphology patterns essentially differ, and wherein the potential VCLAT is declared an AJR when current and past morphology patterns are essentially similar.

\* \* \* \* \*